United States Patent [19]

Brasey

[11] Patent Number: 4,778,798
[45] Date of Patent: Oct. 18, 1988

[54] PHARMACEUTICAL COMPOSITIONS HAVING VASODILATING AND ANTIANOXIC ACTIVITIES

[75] Inventor: Pierre-Noel Brasey, Communy, Switzerland

[73] Assignee: Seuref A.G., Vaduz, Liechtenstein

[21] Appl. No.: 892,247

[22] Filed: Jul. 31, 1986

[30] Foreign Application Priority Data

Aug. 2, 1985 [CH] Switzerland .................. 3344/85

[51] Int. Cl.$^4$ .................. A61K 31/12; A61K 31/435; A61K 31/125
[52] U.S. Cl. .................. 514/277; 514/688; 514/690; 514/692
[58] Field of Search .......... 514/688, 692, 690, 277

[56] References Cited

U.S. PATENT DOCUMENTS 4,599,232 7/1986 Bertelli ........................ 514/690

OTHER PUBLICATIONS

Merck Index, 9th Ed, C197f, pp. 848–849.

Primary Examiner—Stanley J. Friedman
Attorney, Agent, or Firm—Bucknam and Archer

[57] ABSTRACT

Pharmaceutical compositions having vasodilating and antianoxic activities containing an ubiquinone or Coenzyme $Q_{10}$ and a vasodilating compound selected from the groups of ergotamine, Rauwolfia, vincamine alkaloids, calcium antagonists, $\beta$-blockers, papaverine, Ginkgo biloba, xanthine derivatives, ACE inhibitors, cyclospasmol.

3 Claims, No Drawings

PHARMACEUTICAL COMPOSITIONS HAVING VASODILATING AND ANTIANOXIC ACTIVITIES

The present invention relates to pharmaceutical compositions containing a combination of a ubiquinone coenzyme and one or more compounds having vasodilating activity.

Preferred ubiquinone coenzyme according to the invention is ubiquinone $Q_{10}$, whilst the vasodilators which may be used are selected from the group comprising dihydroergocristine, dihydroergotoxine, nicergoline, vincamine, vincamone, flunarizine, cinnarizine, diltiazem, nicardipine, nifedipine, nimodipine, atenolol, sotalol, captopril, raubasine, cyclospasmol; papaverine, xanthine and Ginkgo biloba derivatives.

The ubiquinone component and the vasodilators are present in the combination in ratios ranging from 1:100 to 100:1, preferably from 10 to 1,000.

The compositions according to the present invention exert an effective therapeutic action in the prevention and treatment of pathological conditions related to cerebral vascular and metabolic impairments, such as those which may occur in atherosclerosis, hypertension, senescence or consequently to vasal spasms.

The biochemical role of Coenzyme $Q_{10}$ is the control of mitochondrial respriation known since a long time (Morton R. A.—Nature 182—1764—1958).

The relationship between lacks in Coenzyme $Q_{10}$ and specific morbid conditions such as myocardiac insufficiency, hypertension and nervous disorders in also known (Folkers K., Littarru G. P., Ho L., Runge T. M., Cooley D.—Int. J. Vit. Res., 40—380—1970).

Exogenous administration of Coenzyme $Q_{10}$ led to the remission of great part of the symptomatology of said pathological conditions (Yamasawa Y.—Biomedical and Clinical Aspects of Coenzyme Q—Elsevier—North Holland Ed., Vol. 2—Pag. 333—1980).

Coenzyme $Q_{10}$ proved to have a therapeutic effectiveness mainly in those disorders related to an impaired tissular oxygenation.

Coenzyme $Q_{10}$ proved in fact to very useful in the treatment of myocardiosclerotic disorders and coronary insufficiency (Folkers K., Wolaniuk A.—Drug Eptl. Res. 10-7-513—1984).

Moreover, in case of poor vascularization, Coenzyme $Q_{10}$ can protect tissues from injuries caused by lipoperoxides or superoxides (Littarru G.P., Lippa S.—Drugs Eptl. Res., 10-7-491—1984).

The pharmaceutical compositions according to the invention besides comprising Coenzyme $Q_{10}$, which exerts a metabolically healing action, correcting disorders due to tissular hypoxia related to a poor vascularization, also contain one or more components selected from the group of vasodilators, which promote and restore a normal tissular oxygenation.

The combination of the invention, containing Coenzyme $Q_{10}$ and a vasodilator selected from the above cited group, proved to be surprisingly more active in treating disorders due to a poor tissular blood flow than what expected the simple addition of the actions of Coenzyme $Q_{10}$ and vasodilator.

This surprisingly synergetic effect was evidenced in different tests, the tolerance and toxicity limits being unchanged in comparison to those of the single drugs.

The results obtained in the pharmacological tests carried out with the combinations of Coenzyme $Q_{10}$ and flunarizine, vincamine, nicergoline, dihydroergocristine and raubasine in comparison with the single drugs, are reported hereinbelow.

The cerebral anoxic conditions of rabbits placed in an impermeable cage in which air was replaced by nitrogen, were measured by means of electroencephalogram (till total electric silence: flat E.E.G.).

Combination of Coenzyme $Q_{10}$ (200 mg/kg per os) and flunarizine (50 mg/kg p.o.) or vincamine (50 mg/kg p.o.) induced a remarkably higher increase in the time required to evidence cerebral anoxia as well a more significant reduction in the time required to restore a normal E.E.G. than those obtained using Coenzyme $Q_{10}$ or flunarizine or vincamine alone. The times of resistance to anoxia were about 10% higher than those of the controls for flunarizine, and 20% in the cases of Coenzyme $Q_{10}$ and vincamine, and became higher than more than 100% when flunarizine or vincamine were combined with Coenzyme $Q_{10}$.

The same synergism was evidenced when Coenzyme $Q_{10}$ was combined with nicergoline, dihydroergocristine or raubasine.

A similar synergism was noticed for the time required to restore the electroencephalographic activity, which was about 10% lower than that of controls in the cases of Coenzyme $Q_{10}$ or flunarizine or vincamine alone, and was reduced of more than 50% with combinations thereof, thus proving a greatly shorter functional recovery.

The synergism between Coenzyme $Q_{10}$ and vasodilators was further evidenced in the test on rat tail necrosis after treatment with a vasospastic agent, such as serotonin (5-hydroxytryptamine).

Serotonin sulfate (10 mg/kg) was injected in the tail root of a group of rats, part of them served as controls, whilst the others received, besides serotonin, Coenzyme $Q_{10}$ (100 mg/kg per os) or flunarizine (50 mg/kg per os) or a combination of the two drugs, at the same dosages.

The time of appearance of cutaneous dyschromias on the tail, gangrene and necrosis was evaluated 14 days after the beginning of the treatment. The animals treated with the combination of the invention showed no sufference symptoms nor tissular necrosis, whilst in the other groups of animals gangrene and necrosis were already evidenced 5 days after the beginning of the treatment with serotonin.

Therefore, this test also shows the singificant synergism between the two components of the combination.

The capability of Coenzyme $Q_{10}$ to improve the hypotensive effect of the above cited hypotensive drugs was evidenced by means of the test hereinafter described.

Male Wistar rats, made hypertensive by injection of 12.5 mg/kg DOCA (deoxycortiocosterone acetate) and water added with 1% sodium chloride, were used.

Oral daily administration, from the beginning of the hypertensive treatment, of 2.5 mg/kg or Coenzyme $Q_{10}$ or 10 mg/kg of flunarizine showed no effect, whilst the two drugs in combination at the same dosages almost completely inhibited hypertension.

The same strong antihypertensive effect was evidenced using spontaneously. hypertensive rats (Okamoto).

In this case the high arterious pressure (besides 180 mmHg), after oral administration for 10 days, was respectively reduced by 9% by treatment with 10 mg/kg flunarizine, by 11% with 2.5 mg/kg Coenzyme $Q_{10}$ and 28% with the combination flunarizine/Coenzyme $Q_{10}$.

Similar results were obtained when replacing flunarizine with vincamine or diltiazem.

The compositions of the invention are therefore useful in human therapy for the treatment of pathological conditions related to vascularization disorders at the cerebral and peripheral level, of both primary and secondary origin, and latter particularly when due to atherosclerosis, hypertension, senescence or vasal spasms.

The compositions of the invention will be formulated according to conventional techniques, with the usual excipients. For oral administration, Coenzyme $Q_{10}$ and the vasodilating compound(s) may be formulated in form of tablets, capsules, dragees, sugar-coated pills, granulates, syrups, ampoules, containing pharmaceutically acceptable conventional excipients, for example inert diluents such as calcium carbonate, sodium carbonate, lactose, talc, granulating and disgregant agents such as starch, alginic acid, sodium carboxymethylcellulose, binding agents such as gelatin, PVP, gum arabic, starch, and lubricants such as magnesium stearate, stearic acid and talc.

Moreover, liquid pharmaceutical formulations for oral administration will optionally contain suspending, preserving, sweetening, buffer and colouring agents.

Suitable formulations for parenteral administration will be sterile aqueous solutions.

I claim:

1. A method of treating pathological conditions related to vascularization disorders at the cerebral and peripheral level, of both primary and seconary origin, due to atherosclerosis, hypertension, senescence or vasal spasms, which consists of administering to a living subject in need of treatment a composition containing an effective amount of Coenzyme $Q_{10}$ and nifedipine, said Coenzyme $Q_{10}$ and said nifedipine being in the ratio of ranging from 1:100 to 100:1.

2. A pharmaceutical composition having antianoxic and vasodilating activities, containing ubiquinone $Q_{10}$ coenzyme and one vasodilating compound which is a calcium antagonist wherein the vasodilating compound is nicardipine, nifedipine, nimodipine, said coenzyme $Q_{10}$ and said vasodilating compound being in a ratio ranging from 1:100 to 100:1.

3. The pharmaceutical composition according to claim 2 in form of a capsule, a sugar-coated pill, a tablet, a granulate, a syrup, an ampoule and a vial for injectable solutions, for oral or parenteral administration.

* * * * *